United States Patent [19]

Ghiraldi

[11] Patent Number: 5,276,611
[45] Date of Patent: Jan. 4, 1994

[54] MANAGEMENT OF PARAMETERS RELATING TO A DIALYSIS TREATMENT

[76] Inventor: Andrea Ghiraldi, Via Murri 21, 46025 Poggio Rusco - Mantova, Italy

[21] Appl. No.: 646,595
[22] PCT Filed: May 29, 1990
[86] PCT No.: PCT/EP90/00906
§ 371 Date: Mar. 15, 1991
§ 102(e) Date: Mar. 15, 1991
[87] PCT Pub. No.: WO90/14850
PCT Pub. Date: Dec. 13, 1990

[30] Foreign Application Priority Data

May 25, 1989 [GB] United Kingdom ............... 8912071
May 31, 1989 [IT] Italy .......................... 67421 A/89

[51] Int. Cl.$^5$ .......................................... G06F 15/00
[52] U.S. Cl. ........................ 364/413.03; 364/413.02
[58] Field of Search .................. 364/413.01, 413.02, 364/413.03, 413.04, 413.05, 413.06, 413.07, 413.08, 413.09, 413.10, 413.11; 128/670, 671

[56] References Cited

U.S. PATENT DOCUMENTS

| | | | |
|---|---|---|---|
| 4,153,554 | 5/1979 | von der Heide et al. | 210/96 |
| 4,509,047 | 4/1985 | Rhyner | 340/825.23 |
| 4,608,994 | 9/1986 | Ozawa et al. | 128/670 |
| 4,739,492 | 4/1988 | Cochran | 364/510 |
| 4,774,656 | 9/1988 | Quatse et al. | 364/900 |

FOREIGN PATENT DOCUMENTS 0251520 1/1988 European Pat. Off. ..... G06F 15/42

Primary Examiner—Roy N. Envall, Jr.
Assistant Examiner—Stephen R. Tkacs
Attorney, Agent, or Firm—Finnegan, Henderson, Farabow, Garrett & Dunner

[57] ABSTRACT

The method for the management of parameters relating to a dialysis treatment lies in proceeding at least with the following operations in a dialysis machine during a dialysis treatment:

a) selecting a plurality of parameters relating to the dialysis treatment;

b) establishing a plurality of operating conditions regarding the functioning of the the dialysis machine in relation to the progress of the treatment with respect to time and/or to the course of the values of the said parameters in relation to predetermined variation ranges of these parameters;

c) memorizing the values assumed at that moment by a certain number of the said parameters in accordance with the establishment of each one of the operating conditions.

Using this method and the device for its implementation, it is possible to select and memorize a reduced number of significant parameters relating to the progress of a dialysis session with a view to their transmission over a distance.

11 Claims, 3 Drawing Sheets

MANAGEMENT OF PARAMETERS RELATING TO A DIALYSIS TREATMENT

BACKGROUND OF THE INVENTION

1. Field of the Invention

The present invention concerns a method for the management of parameters relating to a dialysis treatment and a dialysis machine capable of implementing such a method.

2. Description of the Related Art

The method and the dialysis machine referred to are particularly, but not exclusively, well suited for dialysis treatments at home where generally no provision is made for using a specialist (doctor or nurse) on a continuous basis for supervising the progress of the treatment session.

It is obvious, at least in theory, that a dialysis machine may be operated on a remote control and continuous basis by means of a receiver device disposed in a centralized control station, by connecting this receiver device to the dialysis machine, for example, through a telephone line.

It has been found that the continuous control of the dialysis machine requires the transfer and storage of an enormous quantity of values over a relatively long period on the order of three to four hours, corresponding to the whole treatment period. The consecutive utilization of the values obtained entails a considerable loss of time, both for the machine and the receiver device, because many values are controlled which probably have not changed over the whole treatment period. The above outline shows the need for making a method available for the management of the parameters relating to a dialysis treatment, which permits a successive transfer and utilization of numerical data in a much shorter time than at present, so as to make it possible to use in a control station a relatively simple and moderately powered operating unit and which is therefore relatively inexpensive.

SUMMARY OF THE INVENTION

An object of the present invention is therefore to propose a method and a dialysis machine which allow the requirements set out above to be met.

This object is achieved by the present invention which concerns a method for the management of parameters relating to a dialysis treatment including a) selecting a plurality of parameters relating to the dialysis treatment;

b) establishing a plurality of operating conditions regarding the functioning of the said dialysis machine in relation to the progress of the treatment with respect to time and/or to the course of the values of the said parameters in relation to predetermined variation ranges of these parameters;

c) memorizing the values assumed at that moment by a certain number of the said parameters in accordance with the establishment of each one of the operating conditions. According to one characteristic of the invention, the method comprises a preliminary operation which lies in choosing from the said selected parameters, the said number of parameters to be kept in the memory.

According to another characteristic of the invention, the operations (b) of establishing a plurality of the functional operating conditions and (c) of memorizing the values assumed by the said parameters lie, in essence, in:

defining, at least for some of the selected parameters, ranges of variations (delimited by respective threshold limits) of their respective values which they may assume during the said treatment;

verifying any possible excesses of the above mentioned threshold limits;

memorizing for each excess of at least one threshold limit by the corresponding parameter, the value assumed at that moment by at least that parameter, this memorizing operation being effected, for example, either whenever the value assumed by at least one of the said parameters deviates from a range of admissible values, or whenever the value of a parameter having deviated from the said range of admissible values reenters the said range.

According to another characteristic of the invention, the operations for establishing a plurality of functional operating conditions and for memorizing the values assumed by the said parameters lie, in essence, in establishing a periodicity for the memorization of the values of the said parameters, and in automatically effecting the said memorization of the values of the said parameters according to the said periodicity.

The present invention relates, moreover, to a dialysis machine characterized in that it comprises:

a) means for selecting a plurality of parameters relating to the dialysis treatment;

b) operating means for establishing a plurality of operating conditions regarding the functioning of the said dialysis machine in relation to the progress of the treatment with respect to time and/or to the course of the values of the said parameters in relation to the predetermined variation ranges of these parameters;

c) means for memorizing the values assumed at that moment by a certain number of the said selected parameters in accordance with the establishment of each one of the operating conditions.

According to one characteristic of the invention, the said memorization means comprise:

first memorization means for memorizing at least for each one of the selected parameters, ranges of variations (delimited by respective threshold limits) of their respective values which they may assume during the said treatment;

second memorization means for memorizing the values assumed by the said parameters under the control of the said operating means which fix the moment of the memorization, determined by possible excesses of the threshold by the values assumed by the said parameters, the said threshold limits having been memorized in the said first memorization means.

Advantageously, the operating means identify the said excess of the said threshold limit either whenever the value assumed by at least one of the said parameters deviates from a range of admissible values or whenever the value of a parameter having deviated from the range of admissible values, reenters the said range.

In accordance with the invention, the memorization means may, moreover, comprise:

third memorization means for memorizing each parameter having deviated from the range of admissible values, the said operating means being capable of erasing the values of the said parameters memorized in the said memorization means when it reenters the said range of admissible values;

fourth memorization means for periodically memorizing, under the control of the said operating means, the values assumed by at least each one of the said selected parameters and, optionally, the value assumed by other parameters relating to the functioning of the said dialysis machine;

fifth memorization means for memorizing the data relating to the memorization and/or the conversion of the said recorded parameters retained by means of the said selection means;

sixth memorization means for memorizing the data relating to those of the said selected parameters which must be kept under the control of the said operating means.

BRIEF DESCRIPTION OF THE DRAWINGS

For a better understanding of the present invention, the latter will be described in a preferred mode of embodiment, merely by way of a non-restrictive example and with reference to the attached drawings wherein.

DETAILED DESCRIPTION

Figure 1:
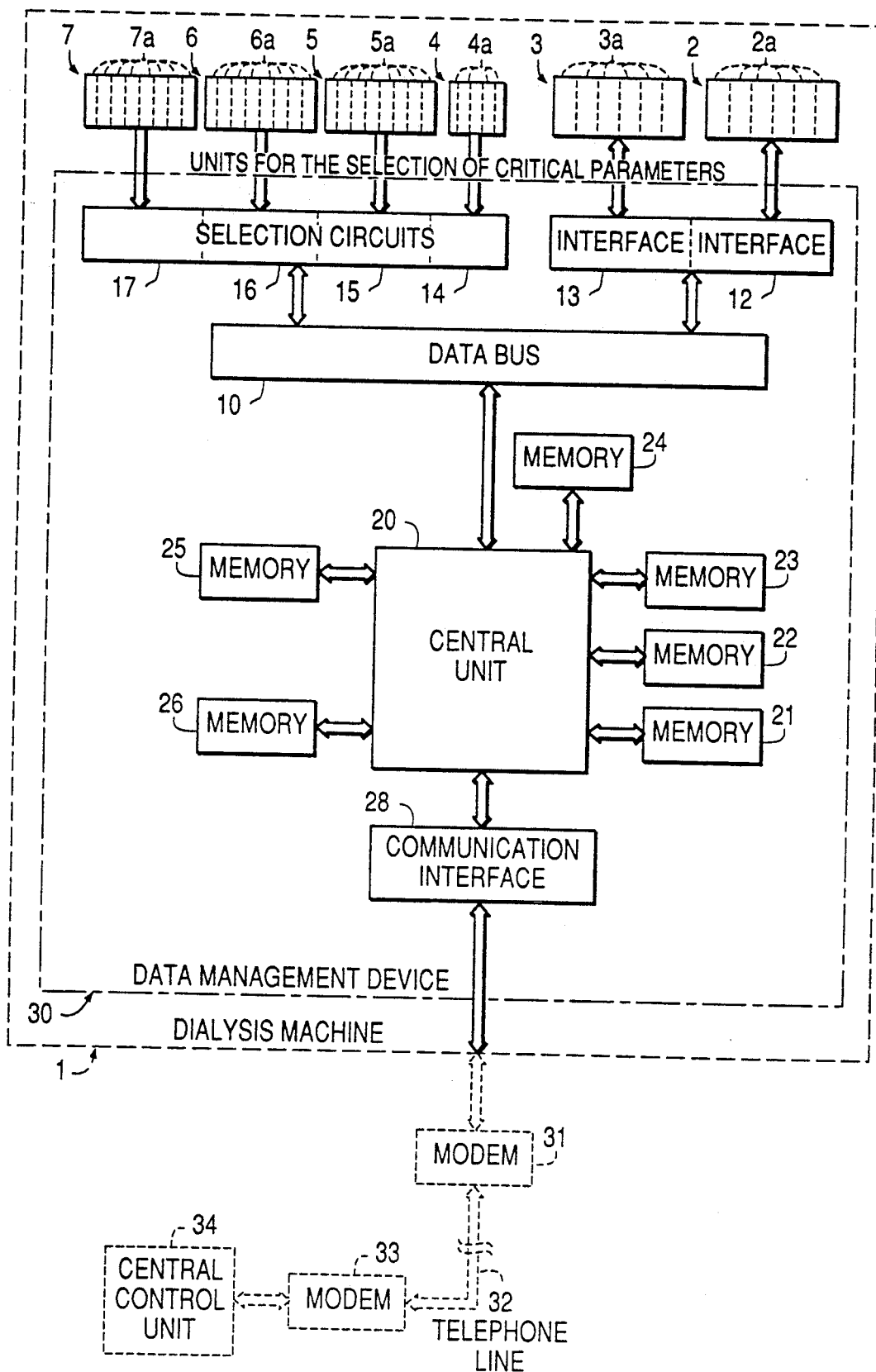
FIG. 1 is a functional block diagram representing a dialysis machine wherein only the elements are shown that relate to the present invention.

Referring more particularly to FIG. 1, the reference numeral 1 designates a dialysis machine as a whole wherein the various devices performing or controlling the dialysis in practice are not shown in as much as they are assumed to be known to the technician.

On the other hand, the units for the selection of the parameters critical for the operation of the dialysis machine 1 are shown, and are assigned the reference numerals 2 to 7.

The units 2 and 3 respectively process the analog and digital type signals and they are, in essence, of the active type, also termed "intelligent" in that they provide values already processed by themselves or by other units not shown (comprising for example, microprocessors disposed at different points of the machine 1). Each unit 2, 3 can process several parameters simultaneously and has, thus, several selection channels indicated respectively by the reference numerals 2a and 3a. By way of example, the parameters selected by the units 2 and 3 could concern the dialysis liquid, (conductivity, temperature etc.) and/or the ultrafiltration device (hourly decrease in the patient's weight etc.).

The units 4, 5, 6, 7 are passive signal selection units respectively of a digital type (units 4, 5) and/or of an analog type (unit 6) and of the type comprising demodulators with a numerical output of signals using any type of representation (for example, modulation of frequency, amplitude, phase, or modulation of the duration, position of the pulses or yet again in general, transformations of spectra, protection or security codes (unit 7).

The unit 4 is preferably constituted by programming microswitches (dip-switches) allowing manual programming of each operational function of the machine 1 by a specialist.

The unit 5 is constituted in essence by a plurality of ON/OFF type sensors capable of indicating the state of a particular parameter (for example, the pressure of the dialysis liquid, a loss of blood etc.) during a dialysis treatment performed by the machine 1.

The unit 6, preferably comprises analog type sensors capable of emitting a signal whose amplitude depends on a corresponding controlled parameter (for example, venous pressure, delivery of a blood pump etc.).

The same considerations apply to the unit 7 whose sensors are capable of generating a modulated or coded signal in accordance with a corresponding parameter.

By way of analogy with the points mentioned above with reference to the units 2, 3, each one of the units 4, 5, 6, 7 processes other parameters and they have selection channels respectively designated by the reference numerals 4a, 5a, 6a, 7a.

The units 2 and 3 already provided with a local processing facility are connected to a data bus 10 by means of respective interfaces 12, 13.

On the other hand, the units 4, 5, 6, 7 are connected to the data bus 10 by means of respective and specific selection circuits 14, 15, 16, 17 basically of the known types. The circuits 14, 15, for example, could comprise a plurality of tri-state type circuits capable of cyclic operation and connected on the one hand, to the above mentioned digital type sensors and on the other hand, to a common multipolar transmission line connected to the data bus 10. The selection circuit 16 could comprise an analog type multiplexer having input terminals respectively connected to analog sensors, and an analog digital converter interposed between the output terminal of the multiplexer and the databus 10. Finally, the circuit 17 has channels, each of which could be constituted by a numerical demodulator having an input capable of receiving a modulated signal generated by the corresponding sensor and an output connected to the data bus 10 by a converter capable of generating a logic-type signal (for example a 16 bit signal).

The data bus 10 is connected to a central operating unit 20, comprising for example, a microprocessor exchanging signals with a plurality of memory devices 21, 22, 23, 24, 25, 26 in accordance with the arrangements set out below. The unit 20 is also connected to a communication interface 28 through which it can hold a dialogue with the outside. Preferably, the interface 28 is provided with a galvanic decoupling device (not shown) with a view to validating, in the case of interconnections with other communication devices (modems) or operating devices scheduled for less stringent conditions, the isolation and elimination of the malfunctions, for which the dialysis machine has been designed.

The circuits 12 to 17, the unit 20 with the corresponding memories 21 to 26 and the serial interface 28 constitute as a whole, a management device 30 (selection, processing, memorizing, transfer) of the signals corresponding to the parameters relating to a dialysis treatment, whose operating modes are described below with reference to FIGS. 2 and 3. This assembly is, in normal service, capable of holding a dialogue with a central control unit 34 which is, for example, a remote unit, and uses appropriate telematic interface means such as modulator-demodulator devices 31, 33 and a common telephone line 32.

Figure 2:
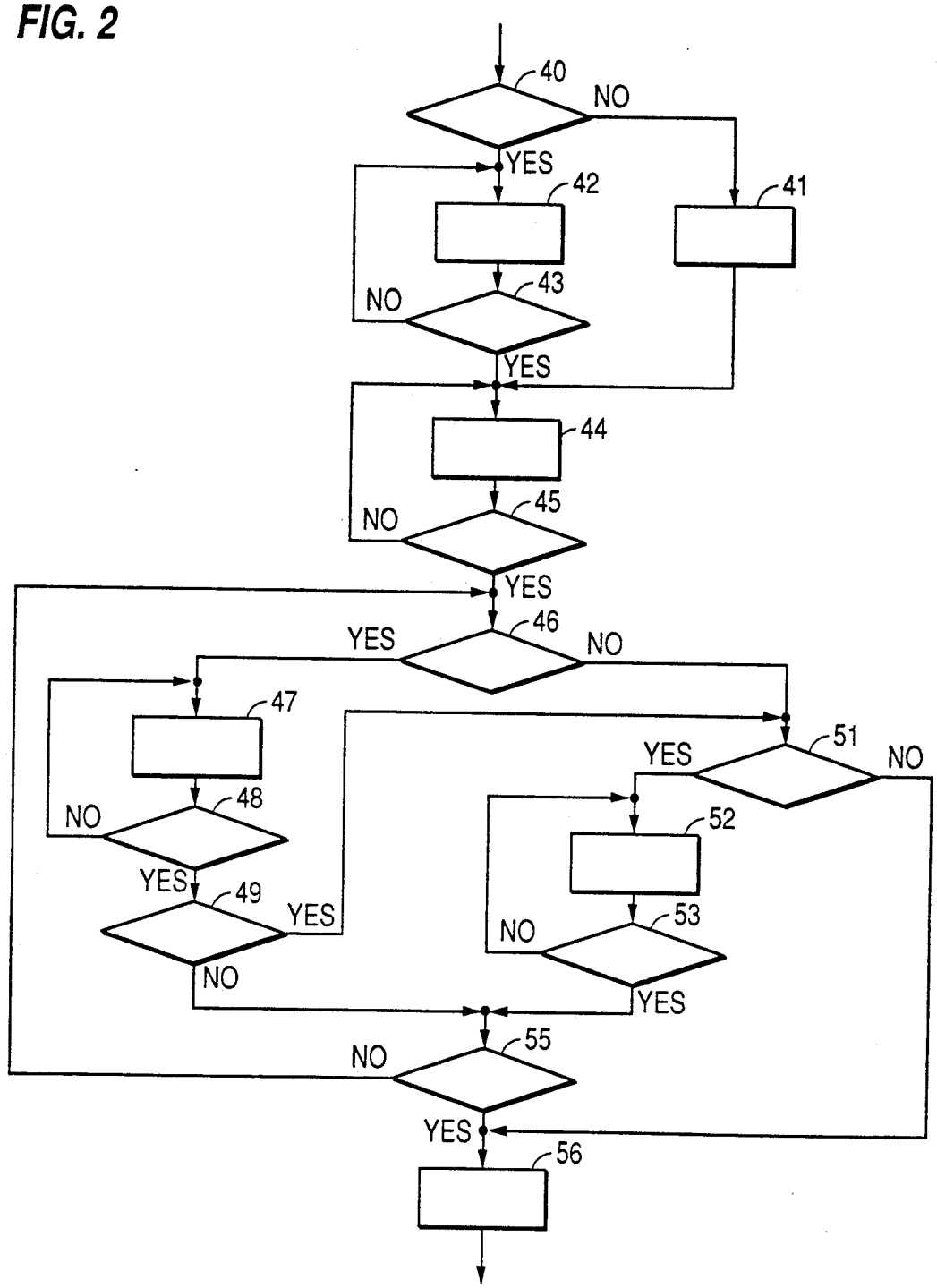
FIGS. 2 and 3 are flow charts of a series of instructions of a preferred mode of embodiment of the main program in an arithmetical operating unit installed in the dialysis machine according to FIG. 1.

FIG. 2 concerns the flowchart for a series of instructions relating to some preliminary adjustments initiated by the operator to prepare the device 30 for operation at the start of the dialysis treatment.

First the block 40 is reached where one checks whether it is intended to set the clock that will subsequently determine the chronology of the selection of values by the device 30. If it is not intended to set the time, the block 41 is reached which attends to the determination of the starting time of the dialysis, for example: hours: 0; minutes: 0; seconds: 0. If it is intended to set a specified time, for example, the time when the treatment will be effectively started, a block 42 is reached provided for effecting such a setting. A block 43 is then reached which checks whether the time has been correctly preset. If not, one returns to the input of block 42 and in the affirmative, one proceeds to block 44 in the same way as from the output of block 41.

Block 44 has the function of making a selection from channels 2a, 3a, 4a, 5a, 6a, 7a of FIG. 1 with a view to keeping only those which will be transversed by any signals of interest meriting a memorization. The block 44 also serves to store the selected channels in the memory 21. Block 45 checks that the selection of these channels is correct. In the case of an incorrect selection, block 45 demands a fresh intervention until the selection is correct.

When the selection is correct, a decision block 46 is reached where the operator's intention to store in the memory 25 any critical dialysis parameters during the dialysis treatment is checked, in particular the conditions or threshold limits of at least one of the selected parameters.

In the affirmative, a block 47 is reached where it is necessary to define for each of the above mentioned channels, a range of admissible values delimiting each range by threshold limits and memorizing the thresholds themselves within the memory 22 of FIG. 1. The correctness of the selection of the threshold limits is checked by means of a block 48 which, in the case of an incorrect selection, demands a fresh intervention at the level of block 47.

When the selection is correct, a verification block 49 is reached checking the operator's intention to effect a periodic memorization of the registered values of the dialysis parameters during the dialysis treatment. If so, one returns to the output of the block 46 and to the input of an additional verification block 51. The latter checks the operator's intention of periodically memorizing some of the parameters stored in the memory 26 during the dialysis treatment.

In the affirmative, a block 52 is reached, by means of which the selection modes and memorization modes of the corresponding parameters are defined for each one of the channels. For example, the values are specified that relate to the frequency of the periodic measurements, to the memory capacity to be used for a memorization in each channel, to optional coefficients for effecting, if necessary, a linear transformation of the registered analog or digital signals etc. All the above mentioned values are stored in the memory 23 of FIG. 1. The check that the above mentioned values have been correctly recorded is effected by means of a block 53 which, in the case of an incorrect recording, demands a subsequent operation causing the block 52 to intervene again.

In the case of a correct arrangement, one arrives in the same way as from the output of block 49 at the input of a block 55 that checks whether at least one operation memorizing the values within the memories 21, 22, 23 of FIG. 1 has been effected. If not, which means that, although a path was followed which provided an operation for the selection and memorization of the values registered for the parameters for the dialysis treatment, no effective operation has taken place (the memories 21, 22, 23, being in fact empty); one therefore returns to the input of block 46. In the affirmative, one arrives at the same time as from the output of the block 51, at a block 56 controlling the start of the dialysis treatment by the machine 1.

Figure 3:
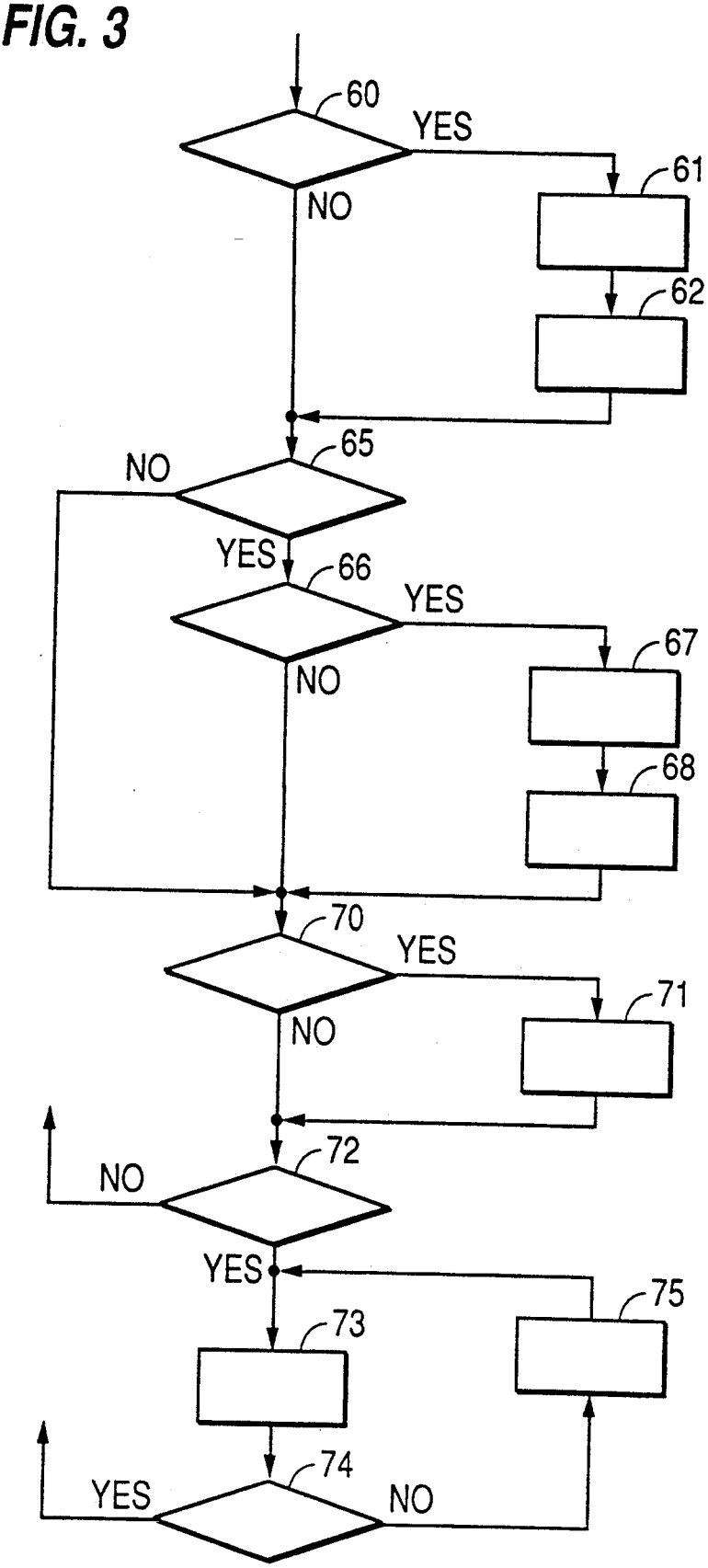

FIG. 3 concerns the flowchart of a series of instructions substantially followed in a cyclic manner by the unit 20 throughout the duration of the dialysis treatment, with a view to registering the values of the selected parameters in the conditions of a particular operation.

First, a comparator block 60 is reached which verifies whether one or several of the selected parameters have a value outside the range of admissible values and which were memorized in the device 22. The comparator block 60 applies a rule of memorization to the data to segregate from the data a subject of data to be stored.

If so, one passes to the block 61 which stores in the memory 25 at least one of the parameters having exceeded a threshold limit defined in the block 47 of FIG. 2 and, moreover, also the date of the event. Merely by way of example, the memory device 25 could be of the circular, or incremental type, so as to permit the memorization of sixty four parameter groups; in this case, the memorization of a sixty fifth would automatically entail the erasure of the one stored in the memory as the first in a chronological order.

The parameter (or parameters) whose value has deviated from the range defined by the threshold limit is subsequently memorized by means of the block 62 within the memory device 24 of FIG. 1, so as to make it possible to control that the value has reentered the range of admissible values.

The above mentioned return is controlled by means of a series of blocks 65, 66, 67, 68. The input of the first of them is reached directly from the outputs of the blocks 60 and 62. In particular, block 65 checks whether there exists at least one parameter stored in the memory 24. If not, one passes to the step defined below with reference to the block 70, whereas in the affirmative one arrives at a comparator block 66 whose function is to check whether the value of the parameter measured at that moment has reentered the range of admissible values or not. The comparator block 66 applies a rule of memorization to the data to segregate from the data a subset of data to be stored.

If not, one passes to the step defined below with reference to the block 70, whereas in the affirmative, a subsequent memorization is effected of the values measured at that moment of at least one of the parameters that has exceeded a threshold limit, as well as of the time of the measurement by means of a block 67, in a way similar to that described with reference to block 61. Subsequently block 68 is reached which determines the abandonment of the parameter whose value has reentered the range of admissible values.

From the outputs of the blocks 65, 66, 68 a comparator block 70 is reached which checks whether the time has come to memorize the processing parameters in accordance with the procedures provided by means of the block 52 of FIG. 2 and stored in the memory 23 of FIG. 1. If not, one proceeds beyond the block 70, whilst in the affirmative, a block 71 is reached which checks that the above mentioned parameters have been stored in the memory 26.

From the blocks 70 and 71, the input of block 72 is reached which searches whether a request has been received via the communication interface 28 of FIG. 1, for transferring the measured values formulated for example, by the central control unit 34. If not, the checks provided in the chart of FIG. 3 are proceeded with, by recommencing with the block 60. In the affirmative, the values are transferred to the unit 34 under the control of the block 73 which orders, for example, the total transfer of the data contained in the memories 25 and/or 26, or the transfer of all the values measured at a given moment for the parameters of the dialysis which have been selected according to the demand formulated by the unit 34 itself.

The check that the transfer has been accomplished is effected by means of the block 74 which, in the affirmative (transfer correctly terminated) provides redirection to the input of block 60, whereas otherwise (transfer in progress or incorrect), it provides redirection to the input of block 73 by means of a buffer block 75 (response analysis).

The operations described above with reference to the blocks 73, 74, 75 are managed by the unit 28, so as to guarantee a reliable data transfer methodology in accordance with a protected protocol, because it is extremely important that the data transfer should be effected in a very reliable manner. A data set could, for example, be passed to intelligent external units which in turn could converse with other intelligent units or retransmit a subsequent set of data to the device 30 with the object of making them available and/or of implementation and/or of interrogation.

The analysis of the management procedure and of the dialysis machine in accordance with the invention clearly demonstrates the advantages that can be obtained.

Above all, it will be observed that the data relating to the most significant occurrences (exceeding the threshold of the range of admissible values) are recorded and made directly available within a quite specific memory zone.

Other data concerning the course of the parameters during the dialysis treatment are selected according to predetermined dispositions (for example periodically) and are also made readily available and transferable from another specific memory zone.

Thus one does not require the use of remote control units provided with high memory capacities and operating means. On the contrary, it will be observed that a control unit with a limited capacity, a microcomputer for example, can thus manage a plurality of dialysis machines (close or remote) effecting simultaneous treatments and which can make the received data available in a central database memory.

The facility of preselecting the parameters to be controlled and/or to be stored in the memory makes it possible to envisage controlled strategies that vary from patient to patient and it renders the use of the dialysis machine equipped in accordance with the present invention very flexible and capable of meeting the most diversified operational requirements.

Finally, it is clear that various modifications and variants may be introduced into the method and the machine described above without departing from the scope of the present invention.

I claim:

1. A method for monitoring a medical treatment, using a control device at a location remote from a place of the medical treatment, the method comprising the steps of:
    monitoring a plurality of parameters of the medical treatment at the treatment place;
    selecting at least one of said plurality of parameters;
    applying a rule of memorization, at the treatment place, to data of the selected parameter to segregate from the data a subset of data to be stored;
    storing, at the treatment place, only the data subset; and
    transferring the data subset to the control device at said location remote from the treatment place.

2. The method of claim 1 wherein the transferring step includes transferring the data subset over a telephone line.

3. The method of claim 1 further comprising the step of defining a rule of memorization prior to applying the rule of memorization.

4. The method of claim 3 wherein the step of defining a rule of memorization includes defining a range of values for the selected parameter so that when data for the selected parameter are within said range then the data within the range are stored.

5. The method of claim 4 wherein the step of defining a rule of memorization further comprises defining the rule to include discarding data of a selected parameter whenever data for the selected parameter are outside of said range.

6. The method of claim 3 wherein the step of defining a rule of memorization includes defining a range of values for the selected parameter so that when data for the selected parameter are outside of said range then the data outside of said range are stored.

7. The method of claim 6 wherein the step of defining a rule of memorization further comprises defining the rule to include discarding data of a selected parameter whenever data for the selected parameter are within said range.

8. The method of claim 3 wherein the step of defining a rule of memorization further includes defining an increment of time, so that data for the selected parameter are stored at time intervals of said time increment.

9. The method of claim 1 wherein the step of selecting a parameter includes selecting a parameter corresponding to an ultrafiltrate flow rate.

10. The method of claim 1 wherein the medical treatment comprises circulating a dialysis liquid through a filter, and the plurality of parameters includes parameters defining characteristics of the dialysis liquid.

11. An apparatus for monitoring a medical treatment, using a control device at a location remote from a place of the medical treatment, the apparatus comprising:
    parameter processing means for monitoring data of a plurality of parameters of the medical treatment, the parameter processing means for placement at the treatment place;
    central processing means for selecting at least one of said plurality of parameters and for applying a rule of memorization to data of the selected parameter to segregate from the data a subset of data to be stored, the central processing means for placement at the treatment place;
    at least one memory unit, for placement at the treatment place, the memory unit for storing only the data subset; and
    means for transferring the data subset to the control device at said location remote from the treatment place.

* * * * *